United States Patent [19]

Thomson et al.

[11] 4,318,990

[45] Mar. 9, 1982

[54] SEPARATION OF PROTEASES FROM FLUIDS

[75] Inventors: Alan R. Thomson, Abingdon; Brynley J. Miles, Cirencester; John C. Caygill, Finchley; David J. Moore, Shirley, all of England

[73] Assignee: United Kingdom Atomic Energy Authority, London, England

[21] Appl. No.: 149,900

[22] Filed: May 15, 1980

Related U.S. Application Data

[63] Continuation of Ser. No. 40,124, May 18, 1979, abandoned.

[30] Foreign Application Priority Data

May 26, 1978 [GB] United Kingdom ............... 23669/78

[51] Int. Cl.$^3$ .................... C12N 9/50; C12N 11/14
[52] U.S. Cl. .................... 435/219; 435/176; 435/183; 435/188; 435/815
[58] Field of Search ............... 435/176, 188, 219, 239, 435/815, 183; 252/455 R

[56] References Cited

U.S. PATENT DOCUMENTS 3,095,358  6/1963  Meister ........................... 435/188 X
3,293,143  12/1966  Heinicke ........................... 435/188
3,850,751  11/1974  Messing ........................... 435/176
3,943,072  3/1976  Thomson et al. ............... 252/455 R

FOREIGN PATENT DOCUMENTS 551339  3/1977  U.S.S.R. ............................. 435/815

Primary Examiner—David M. Naff
Attorney, Agent, or Firm—Larson and Taylor

[57] ABSTRACT

Proteases are separated from fluids by contacting a fluid with a porous inorganic material such as porous titania particles to sorb the protease and then eluting the protease from the inorganic material. Proteases which may be separated are the sulphydryl proteases including papain, stem bromelain, fruit bromelain, ficin, calotropain and mexicain. Elution of the protease may be carried out with plant juice from which protease has previously been removed. The porous inorganic material is preferably that prepared by mixing a finely divided sorptive inorganic material with a solid fugitive additive and a solvent to dissolve the fugitive, forming discrete particles from the resultant mixture and heating the particles to remove the solvent and fugitive to produce discrete particles of the inorganic material for contacting with the fluid.

3 Claims, No Drawings

SEPARATION OF PROTEASES FROM FLUIDS

This is a continuation, of application Ser. No. 40,124 filed May 18, 1979, now abandoned.

The present invention relates to separations and finds application in the separation of proteases.

According to one aspect of the present invention there is provided a process for the separation of a protease from with an inorganic material capable of sorbing the protease thereby to retain and separate the protease from the fluid.

The sorbed protease may be subsequently recovered from the inorganic material, for example by elution with an eluting reagent capable of desorbing the protease.

The eluting reagent may be, for example, a fluid comprising an aqueous solution having a higher pH than the fluid. The eluting reagent may be, for example, an aqueous solution having a higher ionic strength than the fluid. The aqueous solution may be for example an aqueous buffer solution.

The inorganic material is preferably washed after the sorbing of the protease and before elution.

The fluid is preferably an aqueous liquid (e.g. an aqueous solution).

In one embodiment of the present invention the protease is a sulphydryl protease.

We prefer that the inorganic material is a porous inorganic material. Preferably the porous inorganic material is a porous inorganic material having an interconnected porosity throughout which provides an extended surface area and a pore structure such as will allow the protease (e.g. sulphydryl protease) to permeate the material and be sorbed, thereby to separate the protease from the fluid.

Also we prefer that the porous inorganic material is in the form of discrete porous particles.

A preferred form of discrete porous particles for use in accordance with the present invention are those prepared by a method as claimed in any one of claims 1 to 10 of U.S. Pat. No. 3,943,072. (The British Patent Specification corresponding to U.S. Pat. No. 3,943,072 is British Patent No. 1,421,531).

Claim 1 of U.S. Pat. No. 3,943,072 reads as follows:

"A method for producing an inorganic material having interconnected porosity throughout the material for the selective retention of predetermined molecules from a fluid substance containing said molecules including the steps of: mixing a finely divided, substantially insoluble, sorptive, inorganic material capable of sorbing the molecules, with a solid fugitive additive to form a mixture, including in the mixture a solvent to dissolve fugitive additive in the solvent, said inorganic material being substantially insoluble in said solvent, forming discrete particles from the mixture, and heating the particles to remove solvent and fugitive additive to produce discrete particles of said inorganic material having an interconnected pore structure throughout said discrete particles providing an extended surface area, the pore size being such as will allow said predetermined molecules in said fluid substance to permeate the inorganic particles and be sorbed, said inorganic material being substantially unaffected by said heating utilized to effect removal of solvent and fugitive additive."

Discrete porous particles produced in accordance with U.S. Pat. No. 3,943,072 may be substantially spherical and have a size in the range for example of 50–50$\mu$ diameter. The pore structure may contain pores having a diameter in the range 100 to 10000 Å.

Examples of fugitive additives which may be used in accordance with U.S. Pat. No. 3,943,072 are ammonium carbonate, haemoglobin, dextran, polyvinyl alcohol, urea, bovine serum albumin and ovalbumin. Optionally a binding agent may be included in the mixture in addition to the fugitive additive.

Examples of finely divided, substantially insoluble, sorptive inorganic materials which may be used in accordance with U.S. Pat. No. 3,943,072 are titanium dioxide, aluminium oxide, barium sulphate, calcium phosphate, zirconium oxide and calcium sulphate.

The inorganic material may be, for example, conveniently contained in a column (e.g. as a packed bed or a fluidised bed) during contacting with the fluid.

Using discrete porous particles of titania prepared by a method in accordance with U.S. Pat. No. 3,943,072 we have found that proteases may be sorbed in useful quantities from a fluid at various pH values (preferably at pH 8 or less) and in particular we have found that these particles can be used, for example, to sorb proteases at low pH values (i.e. $\leq \sim$pH 5.5).

Sulphydryl proteases (also known as thiol proteases) are proteolytic enzymes which are catalytically active in hydrolysing certain specific peptide bonds where these occur in proteins. This can give rise to polypeptide fragments. These proteases require a reduced sulphydryl group (as well as other less well, or not, known structural features) for their activity. They are suitable for use where relatively rapid but limited (selective) proteolysis is required.

Sulphydryl proteases occur in plants; examples which can be separated in accordance with the present invention are papain (which occurs in the latex of the pawpaw), stem bromelain and fruit bromelain which occur in the stem and fruit respectively of the plants of the Ananas family (e.g. pineapple stem and fruit), ficin (which occurs in the milky latex of the Ficus species), calotropain and mexicain.

It is generally accepted that fruit bromelains of the Ananas family are a series of closely similar proteins of molecular weight of about 31,000 having an isoelectric point of about 4.6, all having basically similar amino acid sequences and conformation.

In principle any fluid containing a protease (e.g. a sulphydryl protease) may be treated in accordance with the present invention to separate the protease. For example, sulphydryl proteases (or derivatives thereof) can be obtained (by techniques known per se) as powders by alcohol or acetone precipitation, and these powders dispersed in water to give a fluid for separation of the protease in accordance with the present invention.

The preparation of such powders, however, can require a number of time consuming and carefully controlled steps and the use of organic solvents with their attendant hazards.

We have found that sulphydryl proteases may be separated in accordance with the present invention directly from fluids obtained from the appropriate plant or part thereof.

Thus, although the present invention can be applied to the treatment of protease-containing fluids produced from plants or parts thereof by a number of routes (e.g. from alcohol or acetone precipitated powders) the present invention offers the advantage of more direct treatment of 'raw' fluids. Thus, plant juices in addition to products derived therefrom may be treated in accordance with the present invention.

The fluid can be obtained, for example, by crushing to give a fluid comprising plant juice (e.g. fruit juice). Fluids may also be obtained, for example, from plant latex. Fluids produced by crushing may be clarified if required by, for example, screening, centrifugation or filtration prior to contacting with the inorganic material.

Plant juice may be obtained, for example, from fruit, or from plant "waste" such as skins or other discarded parts.

In accordance with one particular embodiment of the present invention there is provided a process for the separation of fruit bromelain from pineapple juice which includes the step of contacting pineapple juice with discrete porous particles of titania prepared by a method as claimed in claim 1 of U.S. Pat. No. 3,943,072 whereby fruit bromelain is sorbed from the juice and separated therefrom.

The pineapple juice may be obtained by crushing pineapple fruit, from which the hard top and bottom parts have been removed. The amount of core and outer skin removed prior to crushing can be varied to suit the processing circumstances (e.g. laboratory or in situ in a growing area). Alternatively juice for treating in accordance with the present invention may be obtained from pineapple "waste" (e.g. skins or other discarded parts of the fruit which may, for example, include some juice).

The pH of pineapple juice produced by crushing is usually between 3.4 and 3.8. The juice contains some ions including citrate.

We have found that using discrete porous particles of titania (e.g. in a column) prepared in accordance with claim 1 U.S. Pat. No. 3,943,072 as hereinbefore disclosed it is convenient to wash the particles of titania with alkali, water, acid and then water again to a constant eluate pH (e.g. ~5-6) after which the fluid containing protease to be sorbed may be contacted with the particles.

On contacting titania particles, previously washed as above with pineapple juice we have found that virtually all of the proteolytic activity is sorbed on the particles at the pH of the juice.

The particles may be washed with sufficient water to displace juice from the interstices with substantially no loss of proteolytic activity.

Elution of proteases from porous materials in accordance with the present invention may be affected with a variety of suitable ions. We prefer that these ions are applied in aqueous solution, preferably at a pH>5.0, for example, at pH 7-8, and preferably at a concentration of $\geq 0.1$ M. Such ions may be, for example, citrate, phosphate, pyrophosphate, citrate with added NaCl (e.g. up to 0.5 M). The ions may be derived for example from their salts (e.g. sodium salts such as sodium citrate, etc.) and can be in equilibrium therewith such that the eluting reagent constitutes a buffer solution. Also we have found that, in the case of pineapple juice at least, elution can be effected with protease depleted juice (i.e. with juice from which protease has already been removed, for example, in accordance with the present invention).

The protease depleted juice preferably has its pH adjusted to ~pH 7 to 8 prior to use in elution. Optionally the protease depleted juice can have a salt (e.g. NaCl) added prior to use in elution to raise the ionic strength. It is believed that the presence in the depleted juice of polyvalent ions from the fruit (e.g. citrate which is present in the juice at ~0.03 M) contributes in part to its effectiveness in achieving elution.

In the case of eluting from titania particles fruit bromelain separated from pineapple juice we have found a convenient eluting reagent to be an aqueous citrate solution with a pH of pH $\geq 5$ (e.g. ~pH 7) and a concentration of $\geq 0.1$ M. Preferably the eluting reagent for desorbing fruit bromelain from titania particles comprises $\geq 0.2$ M citric acid/sodium citrate buffer solution.

In accordance with another particular embodiment of the present invention there is provided a process for the separation of papain from a fluid containing papain which includes the step of contacting the fluid with discrete porous particles of titania prepared by a method as claimed in claim 1 of U.S. Pat. No. 3,943,072 whereby the papain is sorbed from the fluid and separated therefrom.

The pH of the fluid containing papain is preferably $\leq 5$. The ionic strength of the fluid is preferably $\leq 0.02$ M.

Elution of sorbed papain is preferably achieved with an aqueous buffer solution with a pH of $\geq 6.5$ and an ionic strength of $\geq 0.2$ M.

In accordance with a further particular embodiment of the present invention there is provided a process for the separation of stem bromelain from a fluid containing stem bromelain which includes the step of contacting the fluid with discrete porous particles of titania prepared by a method as claimed in claim 1 of U.S. Pat. No. 3,943,072, whereby the stem bromelain is sorbed from the fluid and separated therefrom.

The pH of the fluid containing stem bromelain is preferably $\leq 5$ and the ionic strength is preferably $\leq 0.1$ M. or else the ionic strength is preferably $\leq 0.02$ M.

Elution of sorbed stem bromelain is preferably achieved with an aqueous buffer solution with a pH $> 5.0$ and an ionic strength of $\geq 0.1$ M.

In accordance with yet a further particular embodiment of the present invention there is provided a process for the separation of ficin from a fluid containing ficin which includes the step of contacting the fluid with discrete porous particles of titania prepared by a method as claimed in claim 1 of U.S. Pat. No. 3,943,072, whereby the ficin is sorbed from the fluid and separated therefrom.

The pH of the fluid containing ficin is preferably $\leq 5.5$ and the ionic strength is preferably $\leq 0.025$ M, or the pH is preferably $\leq 4.5$.

Elution of the sorbed ficin is preferably achieved with an aqueous buffer solution with a pH of $\geq 5.5$ and an ionic strength of $\geq 0.2$ M.

In accordance with the present invention we have achieved recovery of proteolytic activity of 60% to better than 90%. Also we have achieved improvements of specific activity in some cases, the improvement in particular cases depending upon the eluting ions chosen, the concentration of the eluting solution and the pH value.

The eluted proteases may be recovered from the eluate from the inorganic material, for example, by acetone precipitation, ultrafiltration or freeze-drying. Other suitable processes of recovery may be used.

According to another aspect the present invention provides a protease whenever separated by a process in accordance with the invention.

As separated from fluids derived from plants or parts thereof by use of the present invention the proteases may contain other enzymes. In the case of pineapple fruit bromelain there may be present in the bromelain other enzymes such as acid phosphatase, β-N-acetyl glucose-aminidase (also called acetoamido glucosidase). The relative proportions of these enzymes to each other and to the fruit bromelain need not, and generally will not, be the same as that in the plant.

The protease separated from the fluid may also contain natural activators (e.g. ascorbic acid) from the plant. If desired activators can be added to the protease after separation and recovery by elution; such activators can be, for example, sodium and/or potassium metabisulphite.

The protease separated from the fluid may contain natural fruit acids (e.g. citric acid). In some cases it may be advantageous to recover the citrates from depleted juice to use as an eluent.

The protease separated from the fluid may contain some glucose and possibly other polyols. However, optionally, a stabilising agent or agents may be added to the protease after separation and recovery by elution—examples of such stabilising agents are: glucose, lactose, sorbitol and glycerol. The amounts of stabilising agent required to enable the protease to be stored may be in the region of >10–20% by weight.

Preservatives against microbial attack may be added to the protease after separation and recovery by elution. Such preservatives may be, for example, benzoic acid, sorbic acid or metabisulphite.

According to a further aspect the present invention provides a protease optionally containing one or more of the following:

(i) an activator; (ii) a stabilising agent; (iii) a preservative.

According to yet a further aspect, the present invention provides a protease in the form of a powder.

According to yet a further aspect, the present invention provides, an aqueous protease preparation optionally containing a stabilising agent and/or a preservative.

Table I shows the % of the proteases stem bromelain, ficin and papain sorbed from liquids under various conditions by discrete particles of $TiO_2$ in a column. The $TiO_2$ particles had a particle size of ~250μ and a pore size of 1000–10000 Å, and were prepared in accordance with a method as claimed in claim 1 of U.S. Pat. No. 3,943,072 hereinbefore disclosed.

TABLE I

| Buffer (M Citrate) | pH | % Protease sorbed | | |
|---|---|---|---|---|
| | | Stem Bromelain | Papain | Ficin |
| 0.02 | 4.0 | 100 | 75 | 100 |
| 0.02 | 5.0 | 100 | 68 | 96 |
| 0.02 | 6.0 | 100 | 72 | 83 |
| 0.02 | 7.0 | 99 | 62 | 70 |
| 0.02 | 8.0 | 100 | 68 | — |
| 0.25 | 4.0 | 98 | 57 | 97 |
| 0.25 | 4.5 | 96 | — | 31.2 |
| 0.25 | 5.0 | 67 | 42 | 0 |
| 0.25 | 6.0 | 6 | 20 | — |
| 0.25 | 7.0 | 7 | 17 | 0 |

It will be noted that the amount of protease sorbed decreases with increasing buffer concentration and pH.

Table II shows the % of three proteases eluted from $TiO_2$ particles (of the type referred to in connection with Table I) under various conditions. [5 g $TiO_2$ in column; protein concentration 0.23–0.32%; loaded at 73–150 ml/hr: as follows: stem bromelain (0.02 M Na citrate, pH 7.0), papain (0.01 M Na citrate, pH 7.0), and ficin (0.02 M Na citrate, pH 5.5).]

TABLE II

| Eluting Buffer | pH | % Protease eluted | | |
|---|---|---|---|---|
| | | Stem Bromelain | Papain | Ficin |
| 0.1M Na citrate | 7.0 | 27 | — | 70 |
| 0.1M Na citrate + 0.25M NaCl | 7.0 | — | 46 | — |
| 0.2M Na citrate | 7.0 | 78 | — | — |
| 0.25M Na citrate | 7.0 | 85 | 30 | 78 |
| 0.25M Na phosphate | 7.0 | 88 | — | — |
| 0.25M Na citrate + 0.1M NaCl | 7.0 | — | 61 | — |
| 0.25M Na citrate + 0.25M NaCl | 7.0 | — | 60 | — |
| 0.25M Na citrate + 0.5M NaCl | 7.0 | — | 71 | — |
| 0.25M Na citrate | 5.5 | — | — | 87 |

Table III shows the % of pineapple fruit bromelain eluted from $TiO_2$ particles (of the type referred to in connection with Table I) under various conditions. Prior to elution under the shown conditions, the fruit bromelain had been sorbed onto the $TiO_2$ particles from pineapple juice in each case (pH 3.4–3.8).

TABLE III

| Buffer | pH | % Fruit bromelain eluted |
|---|---|---|
| 0.1M sodium citrate | 6 | 70 |
| 0.1M sodium pyrophosphate | 7 | 66 |
| 0.1M sodium phosphate | 7 | 60 |
| Depleted juice* | 8 | 70 |

*'Depleted juice' was pineapple juice already passed through a bed of $TiO_2$ particles (of the type referred to in connection with Table I) and thus depleted in fruit bromelain)

Using discrete porous particles of inorganic material (e.g. in a column apparatus) enables high flow rates of liquid and eluting reagents to be used and hence reduce processing time and consequently the degree of inactivation of the protease.

The process of the present invention can be operated to sorb proteases at low pH values (e.g. ~3.4 to 3.8) which is likely to stabilise the SH groups of sulphydryl proteases and tend to reduce self digestion. Previous known methods for the separation and isolation of sulphydryl proteases have involved some or combinations of the following features: the use of reagents to complex heavy metals (e.g. EDTA), the use of mercurials to reversibly block and hence protect the thiol groups, the use of reducing agents (e.g. $SO_3$) to maintain free —SH groups. The present invention may be used without recourse to these features.

It is interesting to note that the sorbtion of albumin (which has the same isoelectric point (pI ~4.6) as pineapple fruit bromelain) is very low on $TiO_2$ particles of the type referred to in connection with Table 1, especially in the presence of low concentrations of polyvalent ions (e.g. phosphate).

It is further known that polyvalent ions tend to inhibit sorption on $TiO_2$.

Thus it is surprising that, for example, pineapple fruit bromelain of the same isoelectric point as albumin can be substantially totally sorbed from pineapple juice on substantially similar $TiO_2$ particles at pH 3.4 to 3.8 in the presence of polyvalent citrate ions (0.03 to 0.05 M in 'raw' juice).

The present invention offers the advantage that the inorganic material used for sorbing the proteases is not so liable to microbiological attack and degradation as organic materials such as cellulosic ion-exchangers. This could be significant in certain applications. For example pineapples tend to be grown in large quantities only in the Tropics where problems of microbial growth are severe and organic materials are susceptible to microbiological degradation.

The present invention offers the advantage of enabling the separation of proteases to be separated from fluids at Tropical ambient temperatures.

As hereinbefore stated in connection with Table I the amount of protease sorbed can decrease with increasing buffer concentration. This is shown also in Table IV below showing % stem bromelain sorption on $TiO_2$ particles where the pH was maintained substantially constant and the buffer concentration varied.

TABLE IV

| Buffer (M citrate) | pH | % stem bromelain sorbed |
|---|---|---|
| 0.02 | 5.0 | 100 |
| 0.05 | 5.0 | 99 |
| 0.10 | 5.0 | 99 |
| 0.25 | 5.0 | 66 |
| 0.50 | 5.0 | 19 |

[$TiO_2$ particles were of type referred to in connection with Table I-5 g $TiO_2$ in column; 0.5% stem bromelain in citrate buffer, 5.5 ml fractions of eluate collected and assayed for stem bromelain content. Flow rate 94 ml/hr.]

The invention will now be further described by way of Example only as follows:

EXAMPLE 1

5 g of spheroidal $TiO_2$ particles (mean diameter ~250μ pore size 1000 to 10000 Å prepared in accordance with claim 1 of U.S. Pat. No. 3,943,072 hereinbefore mentioned, were packed in a 15×0.9 cm column which was then washed with several column volumes of water. 10 column volumes (cv) of untreated pineapple juice (pH 3.7) (expressed from pineapples) were passed through the column at 50 ml/hr, and outlet fractions were collected and monitored for milk clotting and caseinolytic activity. All enzyme activity was sorbed under these conditions. The column was then washed with 4 cv water and the enzyme was eluted using 0.1 M citrate pH 8.0, 73% of the caseinolytic activity being recovered in the first 10 mls of eluate.

[The caseinolytic activity was determined using a method substantially similar to that of G. S. Skelton described in "Phytochemistry" 1969, Volume 8, pp 57-60].

The result is shown in Table V below.

EXAMPLES 2-9

The above procedure of Example 1 was repeated several times (using 50 ml juice/experiment), but eluting with different buffers. The results are as shown in Table V below. Clearly a range of eluting buffers may be used, including citrate (0.1-0.25 M), citrate+0.2 M NaCl, phosphate (sodium salts are preferred to potassium salts), hexameta- and pyrophosphates all at pH's >6.5. Surprisingly, juice which has been passed through a $TiO_2$ column to remove bromelain (i.e. depleted juice), is an effective eluant if adjusted to pH ~7-8.

TABLE V

| | Buffer | pH | Flow Rate (ml/hr) | % Recovery (1st 10ml) Enz Act | Protein* | Sp Act Juice | Sp Act Eluate |
|---|---|---|---|---|---|---|---|
| Example 1 | 0.1M Citrate | 8.0 | 50 | 73 | 7.8 | 1.3 | 12.1 |
| Example 2 | 0.1M Citrate | 6.0 | — | 70 | 10.5 | 2.0 | 6.3 |
| Example 3 | 0.1 M Na Phosphate | 7.0 | 60 | 60 | 11.6 | 2.4 | 12.1 |
| Example 4 | 2% Hexametaphosphate | 6.8 | 47 | 56 | 10.6 | 1.3 | 8.8 |
| Example 5 | 0.025M Citrate | 7.0 | 66 | 12 | 3.8 | 1.1 | 3.5 |
| Example 6 | 0.025M Citrate + 0.2M NaCl | 7.0 | 37 | 55 | 7.4 | 1.0 | 7.1 |
| Example 7 | 0.1M Na Pyrophosphate | 7.0 | 43 | 66 | 9.0 | 1.8 | 11.4 |
| Example 8 | Depleted juice (0.7% w/v or 0.03M Citrate) | 8.0 | 69 | 70 | | | |
| Example 9 | Depleted juice + 0.2M NaCl | 8.0 | 53 | 92 | | | |

*estimated from N content - Kjeldahl N × 6.25 method)

EXAMPLE 10

Recovery of Stem Bromelain 10 ml of an 0.5% solution of stem bromelain (containing 46.8% wt/wt protein) in 0.02 M citrate pH 7.0, was loaded on a 5 g $TiO_2$ column (15×0.9 cm), at a flow rate of 60 ml/hr. ($TiO_2$ was as used in Example 1). The column was washed with water (4 cv) and then 0.25 M citrate pH 7 was passed through the column and fractions were collected. Stem bromelain activity determined as in Example 1, was found to have been adsorbed at pH 7, and 84.7% was eluted in the first 10 mls of eluate.

EXAMPLE 11

Recovery of Papain

A 0.5% solution of papain (Powell & Scholefield, spray dried, 50.6% protein), was made up in 0.01 M citrate pH 7.0. 25 ml of this solution was loaded on a 15×0.9 cm column, containing 5 g $TiO_2$ particles (as used in Example 1), at a flow rate of 76 ml/hr. The column was washed with water (4 cv) and then elution was carried out with 0.25 M citrate+0.5 M NaCl pH 7.0. Under these conditions, 71% of the papain activity (determined as in Example 1) was recovered in the first 14 ml of eluate.

EXAMPLE 12

Recovery of Ficin

The procedure of Example 11 was followed. Ficin powder (Sigma containing 63.9% protein) was dissolved to 0.5% in 0.02 M citrate pH 5.5, and 10 ml was loaded onto a 5 g column of $TiO_2$, ($TiO_2$ as used in Example 1) at a flow rate of 92 ml/hr. ~90% of the activity was adsorbed. The column was then washed with water (4 cv) and the enzyme was eluted with 0.25 M citrate pH 5.5, resulting in a recovery of 87.4% of the proteolytic activity (determined as in Example 1) in the first 10 ml of eluate.

EXAMPLES 13-17

A 5 g column of titania particles was prepared as in Example 1. In successive experiments, different volumes of pineapple juice (pH 3.5), were loaded at 81–103 ml/hr. Enzyme was then eluted with 0.1 M citrate pH 7.0 at the same flow rate. Table VI below shows the effect of load on adsorption and recovery of adsorbed enzyme. The final column in the Table refers to total enzyme recovered (determined as in Example 1) including fractions collected following the first 10 ml.

TABLE VI

| Example | Vol juice applied (ml) | Flow rate (ml/hr) | Enzyme Adsorbed (%) | Enzyme eluted (%) 1st 10ml | Enzyme eluted (%) All fractions |
| --- | --- | --- | --- | --- | --- |
| 13 | 2.5 | 103 | 99 | 57 | 68 |
| 14 | 5.0 | 96 | 99 | 48 | 75 |
| 15 | 10.0 | 96 | 92 | 52 | 76 |
| 16 | 25.0 | 97 | 86 | 79 | 99 |
| 17 | 50.0 | 81 | 88 | 60 | 90 |

EXAMPLE 18

Reproducibility of the Process 150 g TiO$_2$ spheres (of the type used in Example 1) were washed in water to remove fines, and were then packed into a column (40×2.6 cm, Pharmacia K25). The column was washed successively with 150 ml 0.1 N NaOH, 150 ml H$_2$O, 150 ml 0.1 N HCl and then water until the pH of the eluate was constant. ~1.5 l of fresh, centrifuged pineapple juice (part of the main process stream from a pineapple cannery) was then loaded on the column under gravity 500 (ml/hr.). After washing with 150 ml water, the column was eluted with 300 ml 0.1 M Na citrate pH 7.0 in 6×50 ml volumes. The 50 ml volumes collected were assayed for proteolytic activity. After each cycle the column was washed with 0.1 N NaOH and 0.1 N HCl and with water as described above. This process was repeated 12 times with the same column and source of juice. The average flow rate obtained was 498 ml/hr. Appropriate fractions containing bromelain activity from each run, were pooled and precipitated by adding 3×volumes of acetone, the precipitate being washed with acetone and dried to constant weight. The yield obtained in the above experiment was 4.4 g solid/liter juice, with a recovery of 66.5% of fruit bromelain activity. The specific activity was 1640 u/gm, the protein content was 10.57% (N×6.25). The results of the 12 successive cycles are given below.

The fruit bromelain activity was determined by the method of G. S. Skelton hereinbefore referred to with the modification that the acid supernatant of the Skelton method was treated according to the method of Lowry et al as disclosed in J. Biological Chemistry (1951) Volume 193 pages 265-275 (O. H. Lowry, N. J. Rosbrough, A. L. Farr and R. J. Randall).

TABLE VII

| Cycle | Volume juice (liters) | Flow rate (mls/hr) | Fruit Bromelain Recovered (%) |
| --- | --- | --- | --- |
| 1 | 1.5 | 498 | 73 |
| 2 | 1.0 | 517 | 74 |
| 3 | 1.5 | 529 | 76 |
| 4 | 1.5 | 640 | 62 |
| 5 | 1.5 | 411 | 67 |
| 6 | 1.5 | 520 | 61 |
| 7 | 1.5 | 463 | 64 |
| 8 | 1.5 | 433 | 61 |
| 9 | 1.5 | 562 | 60 |
| 10 | 1.5 | 491 | 65 |
| 11 | 1.5 | 454 | 74 |
| 12 | 1.5 | 468 | 62 |

EXAMPLE 19

Isolation of Fruit Bromelain on Pilot Plant Scale 363 kg fresh pineapples were cored after the ends had been removed by hand. They were then sliced, the pieces were broken by hand (yield 265 kg), and were then pressed in a conventional fruit press through muslin. The juice thereby expressed was then collected (122 liters), and stored for recovery of bromelain. The juice had a pH of 3.5. All operations were carried out at room temperature. 2×45 liters of juice were loaded in successive runs on a 23 liter bed of porous titania spheres (particle size 425–710μ pore size 1000–10000 Å, column size 130×15 cm) prepared in accordance with claim 1 of U.S. Pat. No. 3,943,072 hereinbefore disclosed, at a flow rate of 4.5 liters/min. In each run the column was then washed with 40 l of water and fruit bromelain was then eluted with 0.25 M citrate pH 7.0 (total volume of eluate collected in each run was 50 liters). The pooled eluate (100 l) was then ultrafiltered in a Romicon hollow fibre unit (H15-43-PM10). The resulting product (400 g) contained 6.98% protein with an activity of 277u bromelain/gm solid≡3972 u/gm protein (determined as in Example 1). 92.7% of the activity in the juice was sorbed, and 92.7% of the sorbed activity was recovered in the eluate before ultrafiltration.

We claim:

1. A process for the separation of stem or fruit bromelain from a fluid which comprises contacting the fluid with porous titania particles capable of sorbing the bromelain, said porous titania particles having an interconnected porosity throughout which provides an extended surface area and a pore structure such as will allow the bromelain to permeate the particles and be sorbed, thereby to separate the bromelain from the fluid, and recovering the sorbed bromelain from the porous titania particles by elution with depleted pineapple juice from which bromelain has already been removed, said porous titania particles having been prepared by the steps of mixing finely divided titania, capable of sorbing the bromelain from the fluid, with a solid fugitive additive to form a mixture, including in the mixture a solvent to dissolve the fugitive additive, said titania being substantially insoluble in said solvent, forming discrete particles from the mixture, and heating the particles to remove the solvent and fugitive additive to produce discrete particles of titania having an interconnected pore structure throughout said discrete particles providing an extended surface area, the pore size being such as will allow said bromelain in said fluid to permeate the particles and be sorbed, said titania being substantially unaffected by said heating utilized to effect removal of said solvent and fugitive additive.

2. A process as claimed in claim 1, wherein the titania particles are washed after sorbing of the bromelain and before elution.

3. A process as claimed in claim 1, wherein the bromelain is sorbed from the fluid at a pH value of 8 or less.

* * * * *